United States Patent
Orita et al.

[11] Patent Number: 5,618,545
[45] Date of Patent: Apr. 8, 1997

[54] SKIN-COSMETIC COMPOSITION

[75] Inventors: Yasutaka Orita, Kumamoto; Hiroyasu Koga, Nagano; Sumitaka Kose, Osaka, all of Japan

[73] Assignee: Nihon Nohyaku Co., Ltd., Tokyo, Japan

[21] Appl. No.: 500,130

[22] Filed: Jul. 10, 1995

[51] Int. Cl.⁶ ................................................. A61K 7/40
[52] U.S. Cl. .................................................. 424/401
[58] Field of Search ....................................... 424/401

[56]  References Cited

U.S. PATENT DOCUMENTS

| 4,118,506 | 10/1978 | Taninaka et al. | 514/440 |
| 4,329,479 | 5/1982 | Yabutani et al. | 549/39 |

FOREIGN PATENT DOCUMENTS

| 31828/93 | 7/1993 | Australia . |
| 2.068.421 | 8/1971 | France . |
| 2.131.037 | 12/1976 | France . |
| 62-175415 | 8/1987 | Japan . |
| 7-53336 | 2/1995 | Japan . |
| 2263234 | 7/1993 | United Kingdom . |

*Primary Examiner*—Carlos Azpuru
*Attorney, Agent, or Firm*—Oliff & Berridge

[57]  ABSTRACT

Disclosed is a skin-food cosmetic composition containing, as the active ingredient, at least one compound of the formula (I):

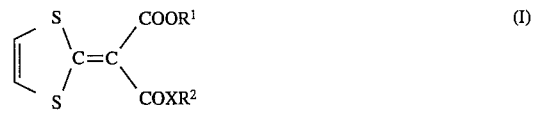

$R^1$ represents an alkyl group having 1 to 10 carbon atoms; $R^2$ represents an alkyl group having 1 to 10 carbon atoms, an alkenyl group having 2 to 6 carbon atoms, or a cycloalkyl cycloalkyl group having 3 to 7 carbon atoms; and X represents —O— or —NH—. This is useful for preventing the skin from being roughened, chapped or cracked, or from being aged.

6 Claims, 1 Drawing Sheet

: P<0.01, * : P<0.001 vs DMSO CONTROL

SKIN-COSMETIC COMPOSITION

BACKGROUND OF THE INVENTION

1. Field of the Invention

The present invention relates to a skin-cosmetic composition useful for preventing the skin from being roughened, chapped or cracked, or from aging.

2. Prior Art of the Invention

Heretofore, various cell activation promoters, such as hyaluronic acid, allantoin and its derivatives, deprotenized bovine blood, extracts from lithospermum roots, extracts from ginsengs, extracts from placentae (various materials extracted from natural substances such as proteins, polysaccharides, extracts:, natural polymers, etc.), etc., have been incorporated into skin-cosmetic materials to be applied to the skin to cure cuts, burns, scalds, etc., for preventing the skin from being chapped, cracked, inflamed or aged, for preventing hemorrhoids, for promoting cell activation in the skin, and for accelerating the healing of wounds on the skin.

However, agents for external use in skin containing theses ingredients having efficacy were not sufficiently effective for the above-mentioned objects, and therefore skin-cosmetic composition having a significantly satisfactory cell-activating effect have heretofore been desirable.

Under the above-mentioned circumstances, the present inventors have assiduously studied to obtain a novel skin-cosmetic composition and have found that compounds of a formula (I):

wherein $R^1$ represents an alkyl group having 1 to 10 carbon atoms; $R^2$ represents an alkyl group having 1 to 10 carbon atoms, an alkenyl group having 2 to 6 carbon atoms, or cycloalkyl group having 3 to 7 carbon atoms; and X represents —O— or —NH—, which are known to be efficacious as pharmaceutical compositions for controlling liver damage of humans and animals in U.S. Pat. No. 4,118,506 and are known to be efficacious as wound healing accelerators in GB-A-2263234 and AU-B-31828/93, have a cell activation promoting effect and are therefore efficacious as "skin-" cosmetic materials for preventing the skin from being roughened, chapped or cracked, or from aging. On the basis of this finding, the present invention has been completed.

SUMMARY OF THE INVENTION

The object of the present invention is to provide a novel skin-cosmetic composition having an active ingredient a compound of the formula (I).

Another object of the present invention is to provide a method for using the compound of the formula (I) for the improvement of preventing the skin from being roughened, chapped or cracked, or from aging.

DETAILED DESCRIPTION OF THE INVENTION

Figure 1:
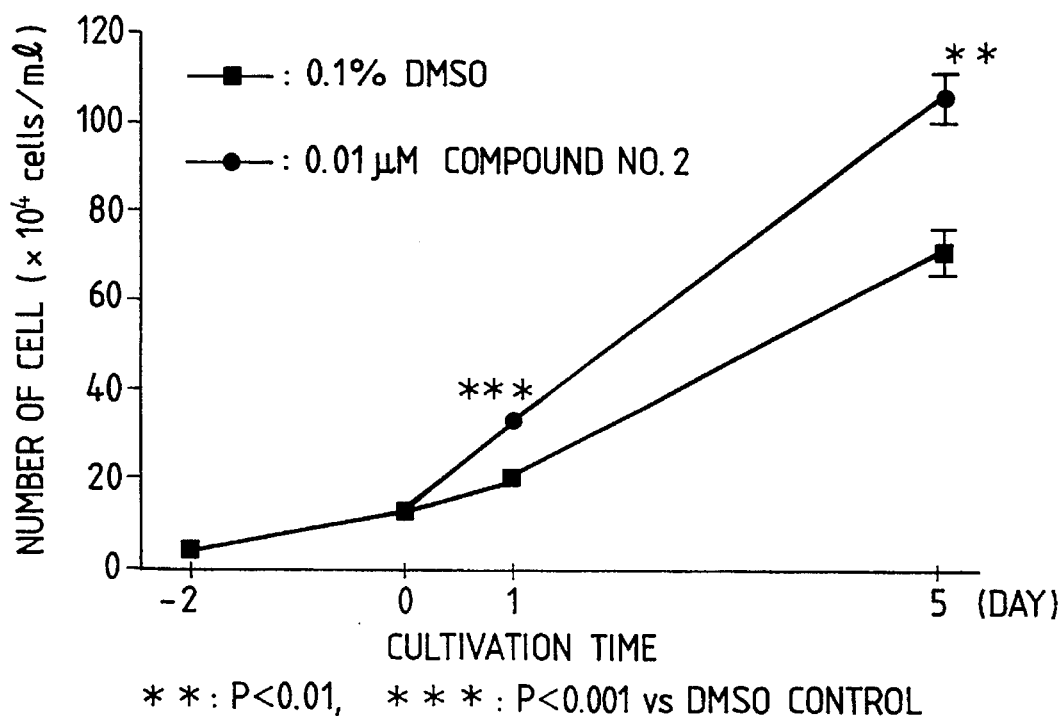
FIG. 1 is a graph showing the relationship between cultivation time and number of cell.

The skin-cosmetic composition of the present invention which contains, as the active ingredient, a compound of the formula (I) has a significant effect of propagating epidermal keratinocytes and also a significant effect of curing skin disorders induced by 12-O-tetradecanoyl phorbol-13-acetate (TPA) and therefore is effective for preventing the skin from being roughened, chapped, cracked or inflamed, or from aging.

It is said that TPA causes skin disorders such as erythema, exfoliation, proliferative hyperacanthosis, etc. and that the symptoms of such disorders are similar to those of dermatokeratonosis as caused by surfactants.

In the above-mentioned formula (I), the alkyl group having from 1 to 10 carbon atoms may be either straight or branched chain and includes, for example, methyl, ethyl, n-propyl, isopropyl, n-butyl, isobutyl, sec-butyl, n-pentyl, isopentyl, neopentyl, n-hexyl and isohexyl groups; the alkenyl group having from 2 to 6 carbon atoms includes, for example, vinyl, allyl, 2-butenyl and 3-pentenyl groups; and the cycloalkyl group having from 3 to 7 carbon atoms includes, for example, cyclopropyl, cyclopentyl and cyclohexyl groups. The alkyl group is preferably an isopropyl group.

Specific examples of the compounds of formula (I) are mentioned below, which, however, are not limitative.

TABLE 1

In the formula (I):

| No. | $R^1$ | $XR^2$ | Data of physical properties |
|---|---|---|---|
| 1 | $CH_3$ | $OCH_3$ | m.p. 125–129° C. |
| 2 | $i\text{-}C_3H_7$ | $O\text{-}i\text{-}C_3H_7$ | m.p. 59–60° C. |
| 3 | $i\text{-}C_3H_7$ | $O-C_2H_5$ | m.p. 54° C. |
| 4 | $i\text{-}C_3H_7$ | O-cyclopentyl | m.p. 69° C. |
| 5 | $i\text{-}C_3H_7$ | $O\text{-}n\text{-}C_6H_{13}$ | m.p. 40° C. |
| 6 | $i\text{-}C_3H_7$ | $O-CH_2CH=CH_2$ | m.p. 48° C. |
| 7 | $i\text{-}C_3H_7$ | NH-cyclopropyl | m.p. 70–72° C. |
| 8 | $i\text{-}C_3H_7$ | $NH\text{-}n\text{-}C_6H_{13}$ | $n_D^{23}$ 1.5728 |
| 9 | $CH_3$ | $O\text{-}i\text{-}C_4H_9$ | $n_D^{20}$ 1.5928 |
| 10 | $C_2H_5$ | $OC_2H_5$ | m.p. 113° C. |
| 11 | $i\text{-}C_4H_9$ | $O\text{-}i\text{-}C_4H_9$ | m.p. 76–78° C. |
| 12 | $i\text{-}C_5H_{11}$ | $O\text{-}i\text{-}C_5H_{11}$ | m.p. 55–56° C. |
| 13 | $n\text{-}C_3H_7$ | $O\text{-}n\text{-}C_3H_7$ | m.p. 73–75° C. |
| 14 | $n\text{-}C_4H_9$ | $O\text{-}n\text{-}C_4H_9$ | m.p. 74–75° C. |
| 15 | $s\text{-}C_4H_9$ | $O\text{-}s\text{-}C_4H_9$ | m.p. 63–65° C. |
| 16 | $n\text{-}C_5H_{11}$ | $O\text{-}n\text{-}C_5H_{11}$ | m.p. 70–70.5° C. |

The skin-cosmetic composition of the present invention may be mixed with the compound of the formula (I) and a base for external use to prepare skin-cosmetic preparations such as skin-emulsions, creams, lotions, powders, agents for pack, cosmetic, liquid, etc.

The content of the active ingredient of the formula (I) in skin-cosmetic preparation may be selected generally from a range of between 0.0001% and 20% relative to the base in the preparation, preferably from a range of between 0.05% and 5% relative to the same, especially preferably from a range of between 0.01% and 3% relative to the same.

The skin-cosmetic composition of the present invention may optionally contain, in addition to the above-mentioned essential components, various additives which are commonly added to ordinary skin-cosmetic preparations, for example, aqueous components which are commonly added to ordinary skin-cosmetic preparations; powdery components such as titanium dioxide, mica, talc, etc.; nonionic surfactants such as polyoxyethylene glycol monooleate, polyoxyethylene alkyl ether, etc.; cationic surfactants such as stearyltrimethylammonium chloride, etc.; anionic surfactants such as sodium palmitate, sodium laurate, alkylsulfate triethanolamine ether, etc.; ampholytic surfactants; humectants such as hyaluronic acid, muco-polysaccharides, glycerin, 1,3-butylene glycol, etc.; higher alcohols such as capryl alcohol, lauryl alcohol, myristyl alcohol, cetyl alcohol; pH-adjustor; thickners such as methyl cellulose, ethyl cellulose, arabic gum, polyvinyl alcohol, montmorillonite, etc.; antimicrobial preservatives such as benzoic acid, salicylic acid, sorbic acid, ethylparaben, butylparaben, hexachlorophene, etc.; higher fatty acids such as capric acid, lauric acid, linolic acid, linolenic acid, etc.; perfumes; oils; dyes; etc.

In addition, the skin-cosmetic composition of the present invention may further contain, if desired, antioxidants such as vitamin E, BHT (dibutylhydroxytoluene), BHA (butylhydroxyanisole), tocopherol, phytic acid, etc.; ultraviolet absorbers such as amyl salicylate, octyl cinnamate, 2, 4-dihydroxybenzophenone, etc.; skin-whitening agents such as ascorbic acid derivatives, hydroquinone derivatives, pyrrones, extracts from bovine placentae, etc.; cell activation promoters such as allantoin and its derivatives, deproteinized bovine blood, kojic acid and its derivatives, adenosine triphosphate, adenosine diphosphate, adenosine monophosphate, succinic acid and its derivatives, extracts from lithospermum roots, extracts from ginsengs, extracts from placentae, etc.

Examples of the present invention are mentioned below, which, however, are not intended to restrict the scope of the present invention. In the examples, all parts are parts by weight.

EXAMPLE 1

| Compound of the invention | 0.5 part |
|---|---|
| Stearic acid | 0.8 part |
| Polyoxyethylene monooleate (20 E.O.) | 1.0 part |
| Bees wax | 2.0 parts |
| Disodium edetate | 0.02 part |
| Bentonite | 0.3 part |
| Concentrated glycerin | 5.0 parts |
| Methyl parahydroxybenzoate | 0.15 part |
| Perfume | ad lib. |
| Pure water | balance |

The above-mentioned components were mixed by an ordinary method to prepare an emulsion.

EXAMPLE 2

| Compound of the invention | 0.1 part |
|---|---|
| Stearyl alcohol | 5.0 parts |
| Cetanol | 5.0 parts |
| Middle-chain fatty acid triglyceride | 10.0 parts |
| Isopropyl myristate | 5.0 parts |
| Polysorbate 60 | 4.0 parts |
| Sorbitan monostearate | 1.0 part |
| Methyl parahydroxybenzoate | 0.14 part |
| Propyl parahydroxybenzoate | 0.06 part |
| Dibutylhydroxytoluene | 0.02 part |
| Pure water | balance |

The above-mentioned components were mixed by an ordinary method to prepare a cream.

TEST EXAMPLE 1

Effect of the Compound of the Invention on the Growth of Human Epidermal Keratinocytes Normal human epidermal keratinocytes (produced by KURABO BIOMEDICAL BUSINESS) were cultured in keratinocyte growth medium (K-GM produced by KURABO BIOMEDICAL BUSINESS; this comprises, as the basal medium, modified MCBD153 and contains epidermal growth factor, bovine pituitary extract, insulin, hydrocortisone, gentamicin and amphotericin B) in humidified atmosphere of 5% $CO_2$ and 95% air for 48 hours at at 37° C. The compound No. 2 of the present invention dissolved in dimethyl sulfoxide (DMSO) was added to keratinocyte basal medium (K-BM) at 0.01 µM, in which the concentration of DMSO was 0.1% of the medium. The number of keratinocytes incubated in the medium containing 0.1% DMSO or 0.01 µM of the compound in the same condition for one day or for 5 days were counted on a hemocytometer. The results are shown in FIG. 1.

The results show that the growth of the cells incubated in the medium containing 0.01 µM of the compound of the invention was significantly increased as compared with that of the cells incubated in the medium containing DMSO.

TEST EXAMPLE 2

Figure 2:
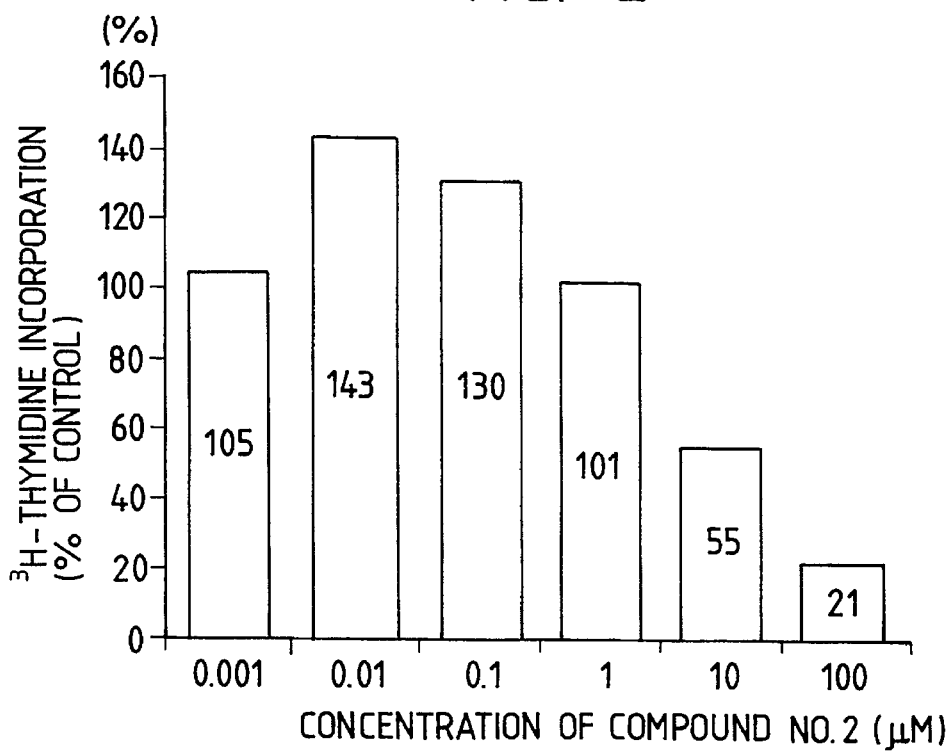
FIG. 2 is a graph showing added concentration of the compound No. 2 of the present invention and incorporation of $^3$H-thymidine to be taken into DNA in cell.

Effect of the Compound on the Growth of Human Epidermal Keratinocytes in the Logarithmic Growth Phase Normal human epidermal keratinocytes suspended in K-GM were seeded in a 12-well culture plate (Costar, 3512) at a concentration of 5×10$^4$ cells/ml/well and cultured in humidified atmosphere of 5% $CO_2$ and 95% air for 48 hours at 37° C. The compound No. 2 of the invention dissolved in DMSO was added to the medium to make a concentration of 0, 0.001, 0.01, 0.1, 1, 10 or 100 µM. The concentration of the respective DMSO was 0.1% of the medium and 0 µM of the compound (0.1% DMSO only) was regarded as the control. The cells were incubated in the medium containing various concentrations of the compound of the invention in the same condition for 24 hours and followed by further incubation in the presence of 2µ Ci of [methyl-$^3$H]-thymidine (NEN, specific activity of 20.0µ Ci/mmol) for 2 hours. After the incubation, 10 µl of 1% $NaN_3$ were added to each culture and cooled with ice, by which the reaction was stopped. The culture was washed two times with a phosphate buffered saline (PBS) containing 1 mM non-ratio labeled thymidine and 0.01% NaN$_3$, and 1.0 ml of 0.2N NaOH was added thereto to lyse the cells. The lysate-containing liquid was taken into a tube and neutralized with 0.2 ml of 1N HCl, and 150 μl of 50% trichloroacetic acid (TCA) solution cooled with ice were added thereto. Then, this was allowed to stand at 4° C. for one full day to form a precipitate therein. The supernatant was removed by centrifugation (at 15000 rpm for 10 minutes), the precipitate was washed two times with a 5% TCA solution, again dissolved in 0.2 ml of 0.2N NaOH and then neutralized with 0.2 ml of 0.2N HCl. The resulting solution (0.2 ml) was put in a vial containing 4.0 ml of a scintillant (Ready Protein$^+$), and its radioactivity was measured a liquid scintillation counting. The incorporation of H-thymidine into the DNA in the cells was represented as a relative value based on the count (100%) per mg of the protein in the cells (or per well) of the control group (0.1% DMSO-added group). Each test was carried out in triplicate, and the average results are shown in FIG. 2.

As compared with control group, the thymidine uptake in the cells of the test group was increased by about 43% in the presence of 0.01 μM of the compound of the invention and by about 30% in the presence of 0.1 μM of the same. However, no change in the thymidine incorporation in the cells was observed in the presence of 0.001 μM or 1 μM of the compound of the invention, while the growth of the cells was oppositely retarded in the presence of the compound of the invention at 10 μM or more.

TEST EXAMPLE 3

Influence of the Compound of the Invention on the Growth of Epidermal Keratinocytes in the Stationary Phase Epidermal keratinocytes suspended in K-GM were seeded in a 12-well culture plate (Costar, 3512) at a concentration of 6×10$^4$ cells/ml/well and cultured in humidified atmosphere of 5% CO$_2$ and 95% air for 48 hours at 37° C. The cells were washed four times with a phosphate buffered saline and then cultured in keratinocyte basal medium (K-BM) at the same condition for 24, 48 or 72 hours. The compound No. 2 of the present invention dissolved in DMSO was added to K-BM to make a concentration of 0, 0.01, 0.1, 1, 10 or 100 μM, in which DMSO concentration in the medium was 0.1%, and 0 μM of the compound (0.1M DMSO only) was regarded as the DMSO control. The cells were incubated in the medium containing various concentrations of the compound in the same condition for 24 hours and followed by further incubation in the presence of 2μ Ci of [methyl-$^3$H]-thymidine (NEN, specific activity of 20.0μ Ci/mmol) for 2 hours. After the incubation, the radioactivity of thymidine in the cells was measured in the same manner as in Test Example 2. During the incubation, each well was observed with a phase contrast microscope (Olympus, IMT-2, phase contrast ULWCD 0.30) at intervals of 24 hours. At the end of the incubation, the total protein content in each well was measured by using a protein-measuring kit (Micro BCA Protein Assay Reagent, Pierce), and the cells in each well were considered to be in the stationary phase at the first point at which the total protein content increased no more. Each test was carried out in triplicate, and the average results are shown in Table 2 below, in which the $^3$H-thymidine incorporation was represented in terms of dpm/well (mean ±S.E.) and the protein content was in terms of μg/well (mean ±S.E.). The statistical analysis of the average values in each group was assessed by Student's t-test. The results are shown in Table 2.

TABLE 2

| Incubation on K-BM | Concentration of the compounds of the invention in the medium (μM) | Incorporation of $^3$H-thymidine (×10$^5$ dpm/well) | Amount of Protein (μg/well) |
|---|---|---|---|
| 24 h + (26 h) | Non-treated control | 16.9 ± 0.6 | 1905 ± 46 |
| | 0.1% DMSO control | 16.7 ± 0.1 | 1892 ± 29 |
| | 0.001 | 16.3 ± 0.2 | 1888 ± 31 |
| | 0.01(*) | 17.9 ± 0.4 | 1900 ± 54 |
| | 0.1(*) | 14.9 ± 0.5 | 1845 ± 29 |
| | 1.0 | 14.7 ± 1.1 | 1870 ± 62 |
| | 10(*) | 15.0 ± 0.5 | 1909 ± 36 |
| | 100(*) | 15.4 ± 0.4 | 1868 ± 80 |
| 48 h + (26 h) | Non-treated control | 6.6 ± 0.1 | 2442 ± 53 |
| | 0.1% DMSO control | 6.6 ± 0.4 | 2382 ± 45 |
| | 0.001 | 6.8 ± 0.2 | 2444 ± 26 |
| | 0.01 | 6.5 ± 0.2 | 2391 ± 49 |
| | 0.1 | 7.2 ± 0.6 | 2351 ± 139 |
| | 1.0 | 6.1 ± 0.4 | 2403 ± 44 |
| | 10 | 6.0 ± 0.4 | 2337 ± 37 |
| | 100(***) | 1.2 ± 0.0 | 2121 ± 12 |
| 72 h + (26 h) | Non-treated control | 4.5 ± 0.1 | 2493 ± 45 |
| | 0.1% DMSO control | 4.5 ± 0.0 | 2400 ± 80 |
| | 0.001 | 4.4 ± 0.1 | 2427 ± 51 |
| | 0.01 | 4.4 ± 0.1 | 2456 ± 6 |
| | 0.1 | 4.4 ± 0.1 | 2450 ± 92 |
| | 1.0 | 4.5 ± 0.1 | 2510 ± 84 |
| | 10(*) | 3.8 ± 0.2 | 2318 ± 20 |
| | 100(***) | 1.3 ± 0.0 | 2367 ± 83 |

*$P < 0.05$
***$P < 0.001$ vs. 0.1% DMSO control in each incubation

The cells in the non-treated control group and those in the 0.1% DMSO control were determined as confluent at 72 hours after the incubation based on microscopic observation of the cells and no increase in protein content after 48 hours (+26 hours) incubation. Even though the compound of the invention was added to the cells after 72 hours (+26 hours) incubation, the incorporation of $^3$H-thymidine in the cells was not increased. From these facts, it is considered that the compound of the invention does not promote the growth of epidermal keratinocytes which have been in the confluent phase. In general, the cells which have been in the confluent phase and have been completely surrounded with other cells in vitro lose their mobility to be in the G$_0$ phase, and their growth is temporarily stopped. As opposed to these, the growth of transformed cells is not hindered by the contact with other cells while their mobility is not changed, and their dividing ability is not decreased even though the cell density is increased. It is known that cancer cells are not in a single layer but are in aggregate while continuously growing and propagating to have a cell density of several times as large as normal cells. When the compound of the invention is added to epidermal keratinocytes, the cells grow and propagate while they are in the logarithmic growth phase [see Table 2, 24 h (+26 h)]but the compound added does not affect the confluent phase of the cells while the cells grow under the density-dependent control of themselves. For these reasons, it is presumed that the compound of the invention will not promote unlimitedly the growth and the propagation of epidermal keratinocytes.

TEST EXAMPLE 4

The hair on the back of each of male C3H mice was shaved. One mM of TPA was dissolved in 70% ethanol, and 0.1 ml/mouse of the resulting solution was topically applied to the thus-shaven back of each mouse twice a week, totaling four times, at which time, the back exhibited erythema, exfoliation and proliferative hyperacanthosis. Compound No. 2 of the invention was dissolved in 70% ethanol at 1% (w/v), and 0.1 ml/mouse of the resulting solution was topically applied to the back of each mouse daily (6 days/week). 12 days and 15 days after the application, the outward appearance of the skin of each mouse was observed, which revealed that the erythema, exfoliation, etc. of the mice in the test group were relieved as compared with those of the mice in the control group and that the degree of the hyperacanthosis of the mice in the test group was histologically light.

As has been described in detail hereinabove, the active ingredient to be contained in the skin-cosmetic compotion of the present invention has a cell-activation-promoting effect and is characterized in that it acts to promote the growth of cells in the growing phase but does not act on cells in the stationary phase. In addition, the active ingredients act to retard the growth of cells when the cells begin to propagate abnormally or differentiate into different cells. Therefore, the characteristics of the skin-cosmetic composition of the present invention are such that it acts as a promoter to promote the curing, of the skin when the skin needs curing while it acts as an inhibitor to inhibit the abnormal reaction of the skin when some abnormal reaction of the skin is to be inhibited. Accordingly, the skin-cosmetic composition of the present invention is useful as a preventive or remedial agent for preventing the skin from aging or roughened and also for curing roughened skin, such as chapped, cracked or inflamed skin.

While the invention has been described in detail and with reference to specific embodiments thereof, it will be apparent to one skilled in the art that various changes and modifications can be made therein without departing from the spirit and scope thereof.

What is claimed is:

1. A method of promoting or propagating epidermal keratinocytes for preventing a skin disorder, said method comprising topically applying to the skin a skin-cosmetic composition containing, as an active ingredient, at least one compound of a general Formula I:

wherein $R^1$ represents an alkyl group having 1 to 10 carbon atoms; $R^2$ represents an alkyl group having 1 to 10 carbon atoms, an alkenyl group having 2 to 6 carbon atoms, or a cycloalkyl group having 3 to 7 atoms; and x represents —O— or —NH—, and wherein said composition contains as an active ingredient 0.0001 to 20% of the at least one compound of the Formula I.

2. The method according to claim 1, wherein the composition is applied in an amount sufficient to prevent the skin from being roughened, chapped or cracked.

3. The method according to claim 1, wherein the skin disorder is selected from the group consisting of erythema, exfoliation and proliferative hypercanthosis.

4. The method according to claim 1, wherein the epidermic keratinocytes that are promoted are in growing phase and wherein the epdirmic leratinocytes that are in stationary phase are not promoted.

5. The method according to claim 1, wherein the skin disorder is induced by 12-O-tetradecanoyl phorbol-13-acetate.

6. The method according to claim 1, wherein the composition is applied in an amount sufficient to prevent the skin from aging.

* * * * *